United States Patent [19]

Evans et al.

[11] Patent Number: 5,019,285
[45] Date of Patent: May 28, 1991

[54] THIOALKANOIC ACID SUBSTITUTED N,N-DIALKYLHYDROXYLAMINES AND STABILIZED LUBRICANT COMPOSITIONS

[75] Inventors: Samuel Evans, Marly, Switzerland; David Chasan, Teaneck, N.J.; Raymond Seltzer, New City, N.Y.

[73] Assignee: Ciba-Geigy Corporation, Ardsley, N.Y.

[21] Appl. No.: 471,167

[22] Filed: Jan. 26, 1990

[51] Int. Cl.$^5$ ............... C10M 133/08; C07C 333/02; C07C 327/22; C07C 321/12
[52] U.S. Cl. .................. 252/47.5; 560/153; 558/253; 558/254; 558/255; 558/251; 564/154
[58] Field of Search ............ 560/153; 252/47.5; 558/252; 564/154

[56] References Cited

U.S. PATENT DOCUMENTS

| | | |
|---|---|---|
| 3,408,422 | 10/1968 | May . |
| 3,644,278 | 2/1972 | Klemchuk . |
| 3,778,464 | 12/1973 | Klemchuk . |
| 4,242,224 | 12/1980 | Dean, II et al. . |
| 4,316,996 | 2/1982 | Collonge et al. . |
| 4,547,532 | 10/1985 | Bednarski et al. . |
| 4,590,231 | 5/1986 | Seltzer et al. . |
| 4,612,393 | 9/1986 | Ravichandran et al. ............ 252/402 |
| 4,720,517 | 1/1988 | Ravichandran et al. ....... 252/51.5 A |

OTHER PUBLICATIONS

*Chemical Pharmaceutical Bulletin,* 27, (1979), Ito et al., p. 1691.
*Tetrahedron,* 26, 5653 (1970) G. Nawson et al.
K. Ito et al., Chem. Pharm. Bull., 27, 1691 (1979).
G. Rawson et al., Tetrahedron, 26, 5653 (1970).

*Primary Examiner*—Prince E. Willis, Jr.
*Assistant Examiner*—Thomas Steinberg
*Attorney, Agent, or Firm*—Stephen V. O'Brien

[57] ABSTRACT

Lubricants are stablized against oxidative degradation by the incorporation therein of hydroxylamines substituted with thioalkanoic acid residues of the formula

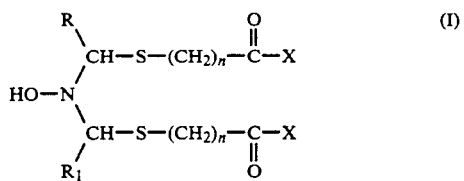

wherein R and $R_1$ are independently H, alkyl or aryl, X is independently $OR_2$, $SR_2$ or $NR_3R_4$ wherein Rhd 2 is H, alkyl, cycloalkyl or aralkyl, and $R_3$ and $R_4$ are independently H, alkyl or aryl and n is 1 or 2.

10 Claims, No Drawings

THIOALKANOIC ACID SUBSTITUTED N,N-DIALKYLHYDROXYLAMINES AND STABILIZED LUBRICANT COMPOSITIONS

FIELD OF THE INVENTION

This invention relates to lubricant compositions which are stabilized against oxidative decomposition by the addition of certain N,N-dialkylhydroxylamines which are substituted with thioalkanoic acid residues. This invention also relates to novel compounds.

BACKGROUND OF THE INVENTION

Various hydroxylamine derivatives have been disclosed as stabilizers for a variety of substrates. U.S. Pat. Nos. 4,720,517 4,612,393, 3,644,278 and 3,778,464 describe the use of substituted hydroxylamines of varying structures as antioxidant stabilizers for hydrocarbons including lubricating oils. U.S. Pat. No. 3,408,422 discloses the use of selected hydroxylamine derivatives in unsaturated polyester compositions to prevent premature gelation on storage. U.S. Pat. No. 4,590,231 discloses the use of N,N-dibenzylhydroxylamine and other selected hydroxylamine derivatives in stabilizing polyolefin compositions. U.S. Pat. No. 4,242,224 discloses that the pink discoloration which occurs in the amine antioxidant and antiozonant emulsions used in the latex industry at high pH can be prevented or retarded by the use of dialkylhydroxylamines or mercaptan stabilizers. U.S. Pat. No. 4,316,996 pertains to a process of preparing phenolic antioxidants in the presence of a hydroxylamine derivative and of a substituted oxime to yield a phenolic antioxidant which itself exhibits improved color and color stability. U.S. Pat. No. 4,547,532 relates to the use of triorganotins and nitrogen compounds including hydroxylamines in the prevention of gelation of paint formulations. Neither the specific hydroxylamine derivatives disclosed herein nor the instantly disclosed lubricant compositions are disclosed in these patents.

Some bis(substituted thioalkyl)hydroxylamines are known. K. Ito et al., Chem. Pharm. Bull., 27, 1691 (1979) describes the Mannich type condensation of selected mercaptans, formaldehyde and hydroxylamine to yield compounds derived from propyl mercaptan, amyl mercaptan, cyclohexyl mercaptan, benzyl mercaptan, thiophenol and ethylene dimercaptan. Related compounds derived from N-methylhydroxylamine, N-benzylhydroxylamine and N-phenylhydroxylamine are also described. G. Rawson et al., Tetrahedron, 26, 5653 (1970) describe the preparation of N,N-(di-p-tolylthiomethyl)hydroxylamine and of N,N'-(di-p-bromophenylthiomethyl)-hydroxylamine in an academic study. No practical use for said compounds is disclosed. The possible use of such compounds as stabilizers for lubricants or other substrates is not suggested or described by the authors who were interested in the possible pharmaceutical applications of said compounds.

SUMMARY OF THE INVENTION

It has now been discovered that certain thioalkanoic acid substituted N,N-dialkylhydroxylamine compounds show surprisingly high stabilizer activity and sufficient solubility in lubricants. The COX moiety provided allows one to modify the compound so as to optimize its compatibility with various substrates.

Thus, the subject matter of the instant invention relates to compounds of formula I and to lubricant compositions comprising a mineral oil, a synthetic oil or mixtures thereof and a stabilizing amount of a compound of formula I

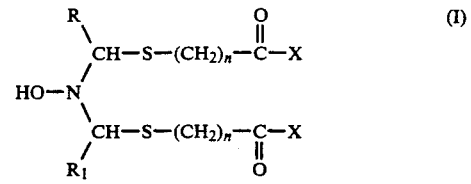

wherein R and $R_1$ are independently H, $C_1$-$C_{18}$-alkyl, or $C_6$-$C_{10}$-aryl, X is independently $OR_2$, $SR_2$ or $NR_3R_4$, $R_2$ is H, $C_1$-$C_{24}$-alkyl, $C_5$-$C_{12}$-cycloalkyl, $C_7$-$C_9$-aralkyl or —$(CH_2CH_2O)_mCH_2CH_2OR_5$ wherein m is 0-6 and $R_5$ is $C_1$-$C_{18}$-alkyl, n is 1 or 2, and $R_3$ and $R_4$ are independently H, $C_1$-$C_{18}$-alkyl or $C_6$-$C_{10}$-aryl.

The various R groups may be $C_1$-$C_{18}$ straight-or branched-chain alkyl, e.g., methyl, ethyl, propyl, isopropyl, n-butyl, isobutyl, n-pentyl, isoamyl, n-hexyl, 2-ethylbutyl, n-octyl, 2-ethylhexyl, isononyl, n-decyl, isoundecyl, n-dodecyl, 2,4-dimethylpentyl, 2,4,6-trimethylheptyl, n-hexadecyl or n-octadecyl. As cycloalkyl, they may also be cyclopentyl or cyclohexyl; as aryl, they may be phenyl or naphthyl and as aralkyl they may be benzyl, α-methylbenzyl or α,α-dimethylbenzyl.

Examples of $R_2$ as polyethyleneoxy are —$(CH_2CH_2O)_3CH_2CH_2OC_6H_{13}$ and —$(CH_2CH_2O)_3CH_2CH_2OC_{12}H_{25}$. Examples of $R_2$ as $NR_3R_4$ are $N(C_8H_{17})_2$ and $N(C_6H_5)_2$.

R and $R_1$ are preferably H. The index n is preferably 1 and $R_2$ is preferably $C_8H_{17}$, e.g. 2-ethylhexyl or isooctyl, or $R_2$ is $C_{13}H_{27}$.

The compounds of formula I can be prepared by the Mannich reaction using an appropriately substituted mercaptocarboxylic acid, hydroxylamine hydrohalide, and an aldehyde. These raw materials are items of commerce or can be prepared by known methods.

The lubricant may be an oil or a grease based on mineral or synthetic fluids. These lubricants are well known to those skilled in the art. The term mineral oil includes all mineral oils used for lubricant purposes, such as hydrocarbon mineral oils. The synthetic fluid may be, for example, an aliphatic or aromatic carboxylic ester or polymeric ester, a polyalkylene oxide, a phosphoric acid ester, polyalpha-olefins, or a silicone. Greases may be obtainable from these by adding metal soaps or other thickeners.

The amount of compound of formula I added to the lubricant depends on the sensitivity of the oil base to oxidation and on the desired degree of protection. Generally, 0.01 to 2% by weight based on the lubricant will be added, and preferably 0.05 to 0.5%.

The compounds of formula I may be used in combination with other antioxidants known as oil additives. Examples thereof are aromatic amines, hindered phenols, aliphatic or aromatic phosphates or phosphites, esters of thiodipropionic or thiodiacetic acid or salts of dithiocarbamic or dithiophosphoric acids. The lubricant composition may also contain other additives, such as metal-passivating agents, rust inhibitors, viscosity regulators, pour point depressants, dispersing agents or detergents, said additives being widely known and used in lubricants.

The following examples will further illustrate the embodiments of the instant invention.

EXAMPLE 1

N,N-bis(2-ethylhexyloxycarbonylmethylthiomethyl)-hydroxylamine

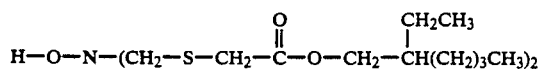

To a stirred suspension of 20.85 g of hydroxylamine hydrochloride in 1200 mL of methanol at 20° C. is added a solution of 20.8 g of potassium hydroxide in 300 mL of methanol. Aqueous formaldehyde solution (36%, 50 g) is added dropwise over a 15 minute period. Then 122.6 g of mercaptoacetic acid 2-ethylhexyl ester are added over a further 15 minute period. The resulting white suspension is filtered and the filter cake is washed with methanol. The combined liquors are then evaporated to give a colorless oil. The oil is taken up in 500 mL of toluene and washed with two 300 mL portions of water. Evaporation of the solvent gives 132.2 g of liquid product.

Analysis: Calc'd. for $C_{22}H_{43}NO_5S_2$: C, 56.7; H, 9.3; N, 3.0; S, 13.8; Found: C, 56.3; H, 9.4; N, 3.0; S, 13.8.

EXAMPLE 2

N,N-bis(isooctyloxycarbonylmethylthiomethyl)hydroxylamine

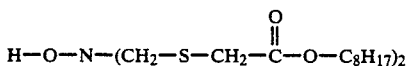

To a stirred suspension of 20.85 g of hydroxylamine hydrochloride in 1200 mL of methanol at 20° C. is added a solution of 20.8 g of potassium hydroxide in 300 mL of methanol. Aqueous formaldehyde solution (36%, 50 g) is added dropwise over a 15 minute period. Then 122.6 g of thioglycolic acid 2-isooctyl ester (prepared from a mixture of $C_8$ alcohols) are added over a further 15 minute period. The resulting white suspension is filtered and the filter cake is washed with methanol. The combined liquors are then evaporated to give a colorless oil. The oil is taken up in 500 mL of toluene and washed with two 300 mL portions of water. Evaporation of the solvent gives 132.2 g of liquid product.

EXAMPLE 3

Minimization of Coke Formation in Aircraft Turbine Oil

The following example illustrates the coke reducing activity of the instant stabilizers.

Stabilizers are blended into the base formulation at the indicated concentrations and tested according to the Federal Test Method No. 791B 3462. This method is used to determine the tendency of finished oils to form coke (solid decomposition products) when in contact with surfaces at elevated temperatures for relatively short periods. It consists of mechanically splashing the oil against a preheated plate under the following prescribed conditions:

| | |
| --- | --- |
| Time | 24 hr. |
| Panel Temperature | 340° C. |
| Oil Splasher Shaft Speed | 1,000 rpm |
| Sump Temperature | 150° C. |
| Air Temperature | 300° C. |
| Air Flow | 1L/min. |

| | |
| --- | --- |
| Base Formulation | Formulated, synthetic, 5 centiStoke., Aircraft Turbine Engine Lubricating Oil (ATO) |

TABLE 1

| Composition | Concentration of Stabilizer | mg of Coke Deposited |
| --- | --- | --- |
| Base Formulation | — | 394.8 |
| Base Formulation + Stabilizer (Example 1) | 0.3% | 112* 104 |
| Base Formulation + Stabilizer (Example 2) | 0.3% | 120 108 |

*Multiple results are indicative of multiple test runs.

It is clear from the data above that small amounts of the instant stabilizer significantly reduce the level of coke formation in commercial jet turbine oil.

Furthermore, the superior activity of the instant stabilizer over a prior art compound exemplified in U.S. Pat. No. 4,720,517 is indicated in Table 2.

TABLE 2

Comparison of Examples 1 and 2 with Prior Art Compound in Degree of Coke Formation

| Composition | Concentration of Stabilizer | mg of Coke Deposited |
| --- | --- | --- |
| Base Formulation | — | 210 |
| Base Formulation + Compound of Example 1 | 0.1% 0.3% | 150.8 70.5 |
| Base Formulation + Compound of U.S. Pat. No. 4,720,517* | 0.3% | 218.3 |

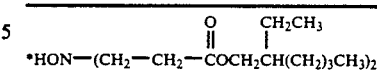

What is claimed is:

1. A compound of formula I

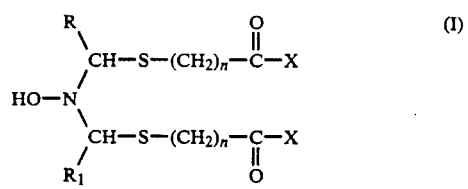

wherein R and $R_1$ are independently H, $C_1$-$C_{18}$-alkyl, or $C_6$-$C_{10}$-aryl, X is independently $OR_2$, $SR_2$ or $NR_3R_4$, $R_2$ is H, $C_1$-$C_{24}$-alkyl, $C_5$-$C_{12}$-cycloalkyl, $C_7$-$C_9$-aralkyl, or —$(CH_2CH_2O)_mCH_2CH_2OR_5$ wherein m is 0–6 and $R_5$ is $C_1$-$C_{18}$alkyl, n is 1 or 2, and $R_3$ and $R_4$ are independently H, $C_1$-$C_{18}$-alkyl or $C_6$-$C_{10}$-aryl.

2. A compound according to claim 1 wherein R and $R_1$ are H.

3. A compound according to claim 2 wherein $R_2$ is $C_8$-alkyl and n is 1.

4. The compound according to claim 1 which is N,N-bis(2-ethylhexyloxycarbonylmethylthiomethyl)hydroxylamine.

5. The compound according to claim 1 which is N,N-bis(isooctyloxycarbonylmethylthiomethyl)hydroxylamine.

6. A lubricant composition comprising a mineral oil or a synthetic fluid or mixtures thereof and an effective stabilizing amount of a compound of formula (I)

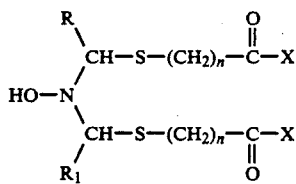

(I)

wherein R and R₁ are independently H, $C_1$-$C_{18}$-alkyl, or $C_6$-$C_{10}$-aryl, X is independently $OR_2$, $SR_2$ or $NR_3R_4$, $R_2$ is H, $C_1$-$C_{24}$-alkyl, $C_5$-$C_{12}$-cycloalkyl, $C_7$-$C_9$-aralkyl or —$(CH_2CH_2O)_mCH_2CH_2OR_5$ wherein m is 0–6 and $R_5$ is $C_1$-$C_{18}$alkyl, n is 1 or 2, and $R_3$ and $R_4$ are independently H, $C_1$-$C_{18}$-alkyl or $C_6$-$C_{10}$-aryl.

7. A lubricant composition according to claim 6 containing a compound of formula I wherein R and R₁ are H.

8. A lubricant composition according to claim 7 containing a compound of formula I wherein $R_2$ is $C_8$-alkyl and n is 1.

9. A lubricant composition according to claim 6, wherein the compound of formula I is N,N-bis(2-ethylhexyloxycarbonylmethylthiomethyl)hydroxylamine.

10. A method of stabilizing lubricants against oxidative degradation which comprises adding thereto an effective stabilizing amount of a compound of formula I according to claim 1.

* * * * *